(12) United States Patent
Miraftab et al.

(10) Patent No.: US 8,563,702 B2
(45) Date of Patent: Oct. 22, 2013

(54) COMPOSITE FIBRE OF ALGINATE AND CHITOSAN

(75) Inventors: Mohsen Miraftab, Bolton (GB); Gillian Mary Smart, Bolton (GB)

(73) Assignee: The University of Bolton Education Corporation, Bolton (GB)

( * ) Notice: Subject to any disclaimer, the term of this patent is extended or adjusted under 35 U.S.C. 154(b) by 619 days.

(21) Appl. No.: 12/279,818

(22) PCT Filed: Feb. 15, 2007

(86) PCT No.: PCT/GB2007/000537
§ 371 (c)(1),
(2), (4) Date: Oct. 2, 2008

(87) PCT Pub. No.: WO2007/093805
PCT Pub. Date: Aug. 23, 2007

(65) Prior Publication Data
US 2009/0099353 A1   Apr. 16, 2009

(51) Int. Cl.
*C07H 5/04* (2006.01)
*C07H 5/06* (2006.01)
*C08B 37/00* (2006.01)

(52) U.S. Cl.
USPC .................................. 536/18.7; 536/55.3

(58) Field of Classification Search
None
See application file for complete search history.

(56) References Cited

FOREIGN PATENT DOCUMENTS

| WO | WO 01/55220 A1 | 8/2001 |
|----|----------------|--------|
| WO | WO 2004/078063 A2 | 9/2004 |

OTHER PUBLICATIONS

Knill et al. Carbohydrate Polymers 55 (2004) 65-76.*
Iwasaki et al. JP 2002-291461. 2002.*
International Search Report PCT/GB2007/000537 dated Dec. 6, 2007 (3 pages).
Hiroshi Tamura et al., "Preparation of Chitosan-Coated Alginate Filament", 2002 (pp. 143-147).
Shyh Ming Kuo et al., "Evaluation of Alginate Coated Chitosan Membrane for Guided Tissue Regeneration", 2005 (pp. 4878-4881).
Database WPI Week 200621, Derwent Publications Ltd., London, GB; AN 2006-194986 XP002435163 & CN 1 687 499 A (Univ Wuhan) Oct. 26, 2005 abstract.

* cited by examiner

*Primary Examiner* — Layla Bland
(74) *Attorney, Agent, or Firm* — Husch Blackwell LLP

(57) ABSTRACT

There are provided composite fibers of alginate and chitosan. Also provided are fiber materials methods of producing composite fibers or films and composite films. In one embodiment there is provided a composite fiber of alginate and chitosan suitable for use in wound management products, wherein chitosan polymer is bonded to alginate polymer along the length of the fiber.

10 Claims, 4 Drawing Sheets

COMPOSITE FIBRE OF ALGINATE AND CHITOSAN

The present invention relates to composites, in particular to fibres of alginate and chitosan, and to methods for their production.

Fibres have been extensively used in the healthcare industry, particularly in the field of wound dressing applications because of their many advantageous properties. In particular fibres made from natural sources, especially from polysaccharides, have been considered promising materials for woundcare due to their ability to imbibe aqueous based media and their biocompatibility as well as their softness and ability to be easily fabricated into many different forms of products.

Amongst the most widely used fibres for production of wound dressings are alginate fibres that are composed of the calcium and sodium salts of alginic acid, a copolymer of guluronic and mannuronic acid, that is obtained from brown seaweed. The presence of sodium ions in an alginate dressing together with ionic exchange of sodium ions in wound exudate for calcium ions in alginate suitably results in the formation of a hydrophilic gel that may facilitate wound healing. In addition ionic exchange resulting in calcium ions being delivered from an alginate dressing to the wound may have a homeostatic effect that is considered beneficial. A wide variety of alginate-based dressings are commercially available including Algisite™ (non-woven calcium alginate fibre, Smith & Nephew), Algosteril™ (calcium alginate, Beiersdorf), Kaltocarb™ (calcium alginate fibre, ConvaTec), Kaltogel™ (calcium/sodium alginate gelling fibre, ConvaTec), Kaltostat™ (calcium alginate fibres in non-woven pads, ConvaTec), Melgisorb™ (calcium/sodium alginate gelling fibre, Molnlycke), Seasorb™ (calcium/sodium alginate gelling fibre, Coloplast), Sorbalgon™ (calcium alginate, Hartman), and Sorbsan™ (calcium alginate fibres in non-woven pads, Pharma-Plast/Maersk).

Another polysaccharide that has been recognised as having a potentially useful balance of properties for woundcare applications is chitosan (a polymer consisting of glucosamine and N-acetyl glucosamine residues), a deacetylated derivative of chitin (comprised of N-acetyl glucosamine residues) that may be isolated from crab shells. Although chitosan is more hydrophobic than alginate there have been a number of reports of chitosan having wound healing properties in addition to anti-bacterial activity that would make a wound dressing comprised of chitosan fibres a potentially viable commercial product. However, the high costs and availability of the raw materials, especially those with high purity and suitability for fibre production has limited commercial development. In addition when chitosan fibres are produced from suitable raw materials poor textile processing properties of the resulting fibres may be a major problem.

One approach to overcome these problems is to produce a "core/sheath" fibre of alginate coated with chitosan as described in International Application Number PCT/GB2004/000950. However, the fibres produced by the methods outlined in this application may not have the desired handlability and with the nature and methodology of coating used the uniformity of chitosan distribution on the alginate core may be uncertain for any given length of the fibre. Some parts of the fibre may thus have little or no chitosan present whilst other parts may have excessive amounts. This could hamper processing ability and cause non-uniformity in functional requirements of the fibre i.e. tensile strength, absorbency etc.

Accordingly, the present invention aims to address at least one disadvantage associated with the prior art whether discussed herein or otherwise.

According to a first aspect of the present invention there is provided a composite fibre of alginate and chitosan suitable for use in wound management products, wherein chitosan polymer is bonded to alginate polymer along the length of the fibre.

Suitably, the fibre comprises a bicomponent fibre of alginate and chitosan.

Suitably, alginate and chitosan polymers are bonded to each other along the entire length of the fibre.

Suitably, the chitosan comprises a disrupted chitosan. Suitably, the chitosan comprises a hydrolysed chitosan.

The chitosan may comprise a disrupted, for example hydrolysed, chitosan having a number average molecular weight ($M_n$) of between 1 KDa and 40 KDa, for example around 7 KDa. Suitably, this molecular weight may be determined by GPC chromatographic analysis.

The chitosan may comprise a disrupted, for example hydrolysed, chitosan having a weight average molecular weight ($M_w$) of between 1 KDa and 150 KDa, for example around 32 KDa. Suitably, this molecular weight may be determined by GPC chromatographic analysis.

The chitosan may comprise a disrupted, for example hydrolysed, chitosan having a viscosity average molecular weight ($M_v$) of between 1 KDa and 150 KDa, for example around 26 KDa. Suitably, this molecular weight may be determined by GPC chromatographic analysis.

The term alginate relates to a polymer composed of mannuronate (M) and guluronate (G) monomeric units. An alginate structure is exemplified below.

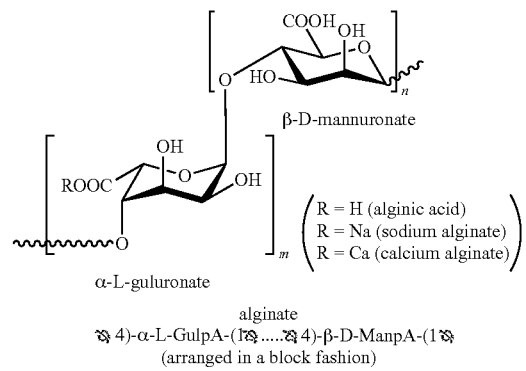

By chitosan it is meant chitosan per se, chitin (fully N-acetylated, only n units as in chitin figure below) and chitan (fully N-acetylated, only m units as in chitosan figure below) and close derivates and salts thereof. Suitably, the chitosan comprises chitosan that has been subjected to a controlled degree of disruption. Suitably, the chitosan comprises hydrolysed chitosan.

Monomeric units of chitin and chitosan are exemplified below.

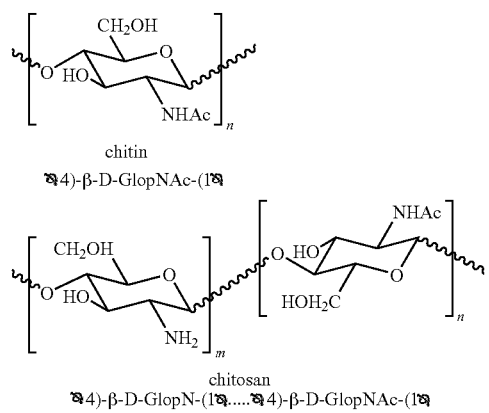

chitin
→4)-β-D-GlopNAc-(1→ chitosan
→4)-β-D-GlopN-(1→.....→4)-β-D-GlopNAc-(1→

The chitosan of the present invention may be acetylated or deacetylated to any degree. By acetylation it is meant the presence or addition of N-acetyl groups and by deacetylation it is meant the absence or removal of N-acetyl groups. The degree of acetylation (DA) is the average number of acetyl groups per monomeric unit i.e. a DA of 0.1 means 1 out of every 10 GlcN residues is acetylated. Chitin has a DA of 1. The degree of deacetylation (DD) is the average number of free amino groups per monomeric unit, i.e. a DD of 0.1 means every 9 out of 10 GlcN units is acetylated. Acetylation and deacetylation can also be expressed as a percentage of the total groups present.

The nature of the chitosan of the present invention may be chosen largely out of consideration for the required properties of the wound management fibre. That said, the chitosan of the present invention may suitably have a DD greater than 50%, for example greater than 70%.

The chitosan fragments suitably have a reduced molecular weight in the range from 1 to 150 kDa.

Disruption may be effected by any suitable means, for example, chemical means. Suitably, it is effected by hydrolytic means.

Hydrolysis of the chitosan material may be achieved by treatment with alkali, but is preferably achieved by treatment with acid.

Suitably, disruption of the chitosan is effected to a significant extent.

The alginate may have a high guluronic ratio, for example it may comprise ManA at 25-35% and GulA at 65-75%. Alternatively, the guluronic ratio may be lower.

Suitably, the fibre comprises both alginate and chitosan polymers throughout its length. The fibre may comprise both alginate and chitosan polymers throughout its cross-section.

The concentration of chitosan may be substantially the same in the centre, mid and outer regions of the fibre. The concentration of chitosan may be substantially constant across the fibres diameter. Suitably, the fibre comprises a homogenous mix of chitosan and alginate polymers throughout.

Suitably, the ratio of alginate:chitosan may remain substantially constant along the fibre length.

The ratio of alginate:chitosan may be between 99:1 and 20:80 by weight. The ratio by weight of alginate:chitosan may for example be between 98:2 and 95:5. Suitably, the ratio by weight of alginate:chitosan is between 70:30 and 30:70, for example between 60:40 and 40:60, for example around 50:50.

Suitably, the fibre comprises chitosan, suitably hydrolysed chitosan, in an amount of between 1% and 80% by weight. Suitably, the fibre comprises alginate in an amount of between 20% and 95% by weight.

The fibre may comprise chitosan in an amount of at least 0.1% by weight, for example at least: 1.0%; 1.5%; 2.0%; 2.5%; 3.0%; 3.5%; 4.0%; or 4.5% by weight. The fibre may comprise chitosan in an amount of at least 5% by weight, for example at least 10%; 15%; 20%; 25%; 30%; 35%; 40%; 45%; 50%; 55%; 60%; 65%; 70%; or 75%.

The fibre may comprise alginate in an amount of at least 20% by weight, for example at least 25%; 30%; 35%; 40%; 45%; 50%; 55%; 60%; 65%; 70%; 75%; 80%; 85%; 90% or 95%.

Suitably, there is provided a bicomponent fibre of alginate and chitosan polymers suitable for use in wound management products, wherein both polymers are bonded to each other along the entire length of the fibre.

Suitably, the fibre is not in the form of a substrate and coating. The fibre may thus not be of a "core-sheath" construction.

The fibre may have improved tensile properties and/or improved liquid absorbency compared to either alginate or chitosan fibres.

Suitably, the fibre can absorb and/or retain at least 10 times its weight of water, for example at least 15 times its weight. Suitably, the fibre can absorb and/or retain at least 10 times its weight of saline solution.

The fibre may comprise a bicomponent fibre of alginate and chitosan that has both good textile processability and is of substantially uniform composition along the length of the fibres produced.

The fibre may be characterised by FT IR spectrum peaks at 1680 cm$^{-1}$, 1720 cm$^{-1}$ and 2878 cm$^{-1}$.

The fibre may be produced with a draw ratio of between 1.00 and 1.30, for example between 1.05 and 1.25.

The fibre may comprise one or more additives to enhance performance and functional requirements. Examples of additives that may be incorporated into the fibre either during the production of the fibre or by subsequent post treatment are antimicrobial agents, agents known to influence wound healing and fragrances.

The fibre may comprise chitosan, suitably modified chitosan, and alginate which are suitably chemically bonded to one another. The fibre may consist of chitosan, suitably modified chitosan, and alginate. Alternatively the fibre may comprise chitosan, suitably modified chitosan, alginate and calcium-alginate.

The fibre of the first aspect may be prepared according to the method of the fifth and/or sixth aspect as described hereinafter. Suitably, the fibre is prepared according to the method of the fifth aspect.

The fibre of the first aspect may comprise any feature as described in relation to the fibre of the second aspect hereinafter.

The fibre may comprise any feature as described in relation to the fibres of the third aspect hereinafter.

According to a second aspect of the present invention there is provided a composite fibre of alginate and chitosan suitable for use in wound management products, wherein the ratio of alginate:chitosan remains substantially constant along the fibre length.

The ratio of alginate:chitosan may be between 99:1 and 20:80 by weight. The ratio by weight of alginate:chitosan may for example be between 98:2 and 95:5. Suitably, the ratio by weight of alginate:chitosan is between 70:30 and 30:70, for example between 60:40 and 40:60, for example around 50:50.

Suitably, the chitosan content of any given length of fibre is substantially the same as that of any other like length of the same fibre. Suitably, the chitosan content of any given 1 cm length of fibre is within 1% by weight of that of any other 1 cm length of the same fibre.

Suitably, the fibre comprises a bicomponent fibre of alginate and chitosan polymers.

The fibre of the second aspect may comprise any feature as described in relation to the fibre of the first aspect.

The fibre may comprise any feature as described in relation to the fibres of the third aspect hereinafter.

The fibre of the second aspect may be prepared according to the method of the fifth and/or sixth aspect as described hereinafter. Suitably, the fibre is prepared according to the method of the fifth aspect.

According to a third aspect of the present invention there are provided composite fibres comprising polysaccharide(s) and/or modified polysaccharide(s).

The composite fibres may comprise polysaccharide(s) and oligosaccharide(s) derived from polysaccharide(s) having a higher molecular weight.

The fibres may be based on alginate and modified chitosan, and may be suitable for use in wound management products.

The fibres may be produced by extrusion of a solution of alginate into a solution of modified chitosan, or vice versa, in a manner which induces insolubility.

The insolubility of the alginate and/or modified chitosan may be induced by alkali, acid and/or calcium ions.

Alginate and modified chitosan in a composite fibre may undergo ionic interaction and this may form a strengthened composite fibre.

The ratio of alginate to modified chitosan in a composite fibre may remain substantially uniform throughout the composite fibre length.

The ratio of alginate to modified chitosan in a composite fibre may remain substantially uniform across the composite fibre radius.

The modified chitosan distribution in the composite fibres may be controlled by control of the molecular weight and/or degree of acetylation of the fragments.

The modified chitosan may be chitosan subjected to molecular weight reduction using a suitable disruptive agent to yield a mixture of chitosan fragments.

The modified chitosan may be chitosan subjected to acetyl content alteration using a suitable agent.

The chitosan fragments may comprise mixed small co-oligomers of glucosamine and N-acetylglucosamine.

The molecular weight of the chitosan fragments may be in a narrow range.

The chitosan fragments may be derived by suitable biological, radiolytic, biosynthetic or chemical means.

The chitosan fragments may be derived by acidic chemical means.

The chitosan fragments may be derived by acidic chemical means using mineral acid and/or organic acid.

The chitosan fragments may be modified by additional chemical treatment.

The chitosan fragments may be modified by additional chemical acetylation and/or sulfation/sulfonation.

The modified chitosan may impart antimicrobial activity to the composite fibres.

Composite fibre polysaccharide components may include carboxymethyl cellulose, pectin, hyaluronan, chondroitin sulfate, maltodextrin, branan ferulate, inulin and/or trehalose.

The fibres may contain antimicrobial agents, such as silver compounds.

The fibres may contain pharmaceutical compounds.

Suitably, fibres according to the third aspect comprise fibres according to the first and/or second aspect.

Fibres according to the third aspect may comprise any feature as described in relation to the first or second aspects.

According to a fourth aspect of the present invention there is provided a fibre material comprising a plurality of fibres according to the first and/or second aspect and/or third aspect.

Suitably, there is provided a fibre material comprising a plurality of fibres according to the first and/or second aspect.

Suitably, the fibre material may comprise a non-woven material, a yarn, a knitted material or a woven material.

Suitably, the fibre material may comprise a wound management material suitable for application to a wound. The wound management material may for example comprise a dressing, gauze or wound dressing pad.

According to a fifth aspect of the present invention there is provided a method of producing a composite fibre of alginate and chitosan, said method comprising the step of extruding a solution of one of alginate or chitosan directly into a bath of the other of alginate or chitosan solution.

Suitably, the alginate solution comprises sodium alginate.

Suitably, there is provided a method of producing a composite fibre of alginate and chitosan, said method comprising the step of extruding a solution of alginate directly into a coagulation bath of chitosan solution.

Alternatively, there may be provided a method of producing a composite fibre of alginate and chitosan, said method comprising the step of extruding a solution of chitosan directly into a coagulation bath of alginate solution.

Suitably, the method comprises extruding a solution of sodium alginate directly into a coagulation bath of chitosan solution comprising chitosan that has been subjected to a controlled degree of disruption.

Alternatively, the method may comprise extruding a solution of chitosan comprising chitosan that has been subjected to a controlled degree of disruption directly into a coagulation bath of sodium alginate.

Suitably, the disruption of the chitosan is achieved by hydrolysis, suitably acid hydrolysis. The method may thus include hydrolysing chitosan to produce disrupted chitosan for use in the fibre forming step. Suitably, the method comprises subjecting chitosan to a controlled degree of acid hydrolysis.

Suitably, the fibre produced comprises a bicomponent fibre of alginate and chitosan.

Suitably, the chitosan employed in the coagulation bath comprises a disrupted, suitably hydrolysed, chitosan having a number average molecular weight of between 1 KDa and 40 KDa, for example around 7 KDa. Suitably, this molecular weight may be determined by GPC chromatographic analysis.

Suitably, the chitosan employed in the coagulation bath comprises a disrupted, suitably hydrolysed, chitosan having a weight average molecular weight of between 1 KDa and 150 KDa, for example around 32 KDa. Suitably, this molecular weight may be determined by GPC chromatographic analysis.

Suitably, the chitosan employed in the coagulation bath comprises a disrupted, suitably hydrolysed, chitosan having a viscosity average molecular weight of between 1 KDa and 150 KDa, for example around 26 KDa. Suitably, this molecular weight may be determined by GPC chromatographic analysis.

Suitably, the alginate solution comprises alginate in aqueous solution in an amount of 0.5 to 10% (w/v), for example 1 to 6% (w/v).

Suitably, the chitosan solution comprises chitosan in an amount of 0.1 to 10% (w/v), for example 0.5 to 5% (w/v).

Suitably, the chitosan solution comprises chitosan in aqueous solution which may further comprise calcium chloride and/or sodium hydroxide in an amount of up to around 2% (w/v).

The chitosan solution may comprise calcium chloride in an amount of between 0.1% and 0.5% (w/v), for example around 0.2% or 0.3% (w/v).

Suitably, the chitosan solution comprises hydrolysed chitosan and may further comprises calcium chloride. Suitably, where calcium chloride is used with a hydrolysed chitosan solution it is added to the chitosan solution after the chitosan has been hydrolysed.

Suitably, the composite fibre formed in the fibre forming step is subjected to a washing operation.

The composite fibre may be washed by being passed through water.

The composite fibre may be washed by being passed through an acetone-water mixture.

Suitably, the composite fibre is washed by being passed through a water bath followed by a number of baths containing acetone-water mixtures to bring about water-solvent exchange within the fibre. This may facilitate drying of the fibre.

Suitably, the fibre is dried, for example using hot air.

Suitably, after drying the fibre is further processed. The fibre may be wound up and may then be further processed. The fibre may for example be processed into non-woven felts or ropes or other structures commonly used for wound management.

Suitably, the fibre produced by the method comprises a fibre according to the first and/or second aspect.

The fibre production method has been described in detail with reference to the extrusion of alginate solution into a bath of chitosan solution. However, it will be appreciated that features relating to the alginate, chitosan and production method may be equally applicable in relation to the extrusion of chitosan solution into a bath of alginate solution.

Suitably, the first stage of the composite fibre production process is to generate chitosan having a controlled degree of deacetylation and purity by carrying out hydrolysis/deacetylation of chitosan under judiciously selected and carefully controlled reaction conditions. The effect of hydrolysis is to suitably cause both depolymerization and deacetylation to a controlled degree.

Suitably, this hydrolysis results in the formation of a range of molecular sizes of chitosan fragments thereby broadening the molecular weight distribution of the polymer. The lowering of the molecular weight of the chitosan may have a major effect on chemical fusion/attraction of the chitosan and alginate at the point of fibre inception.

It may not be possible to form the composite alginate/chitosan fibre in the manner described in this invention using commercially available chitosans of high molecular weight, without first subjecting them to disruption, for example by undergoing prolonged hydrolysis under appropriate conditions.

Although base hydrolysis may be used, it may be preferred that hydrolysis is effected under acidic conditions suitably using a mineral acid, for example hydrochloric acid. The acidic hydrolysis process may involve dissolving 1-6% (w/v), suitably 2-5% (w/v), for example 3-4% (w/v) of chitosan in deionised water suitably in the presence of acetic acid (suitably around 1% v/v). This may be followed by vigorous stirring for 3-4 hours. An aqueous solution of hydrochloric acid having a concentration of 1-5% v/v, suitably 2-4% v/v, for example 3% v/v may subsequently be added and stirring continued to form a homogeneous solution having a pH of between 2-5, for example 3-4. The resulting solution may be heated under reflux for up to 24 hours, suitably for between 4-16 hours, for example 8-10 hours and then cooled.

The chitosan solution thus produced may be used as a bath of coagulating medium for sodium alginate solution which is extruded directly into the chitosan. This extrusion process may result in both polysaccharides chemically fusing together upon contact. This may thus result in the production of a fibre that is constructed from a balanced contribution of both alginate and chitosan at any one point along the entire length of the fibre.

The sodium alginate polymer solutions used to produce the composite fibres of the invention may have a high guluronic ratio (Suitably ManA 25-35%, GulA 65-75%). Alternatively, the guluronic ratio may be lower. Solutions of varying concentration may be used, typically 1 to 6% (w/v), suitably 2-5% (w/v), for example 3-4% (w/v).

The sodium alginate polymer solution is suitably ejected under pressure, suitably of around 20 bar, suitably through a spinneret, into a coagulation bath of chitosan, suitably prepared as described above. The spinneret suitably has a number of apertures of defined diameter, for example 40 to 200 holes suitably with an average diameter of around 50 μm.

Suitably, the alginate solution (dope) is delivered into the chitosan solution, suitably into the hydrolysed bath, at a rate of around 7 cm$^3$/min. The fibre may then be drawn, suitably up to a maximum of 100%, by pick up rollers before being washed. Suitably, the fibre is washed water, for example in lukewarm water (suitably 50-60° C.) and suitably dried by passing through baths of acetone-water mixtures with increasing concentrations of acetone in each bath. Three baths may be used and the first bath may contain around 50% acetone, the second around 70% acetone and the final bath around 100% acetone. This may enable the fibre to be dried using hot air (60-80° C.) as it is wound onto a spool.

A fibre produced by this method may be found to have improved absorption characteristics when compared to alginate or chitosan fibres and to be more robust in terms of force to break in comparison with alginate or chitosan fibres. The tenacity of an alginate/chitosan composite fibre produced according to the method of this invention may lie in the range between 2.8 to 10.5 cN/tex, whereas typical values for calcium alginate fibres may be between 2-10 cN/tex and those for chitosan fibres may be in the range of 1.5-2.5 cN/tex. Alginate/chitosan fibres produced by a core/sheath coating method according to the methods described in International Application Number PCT/GB2004/000950 may have tenacities in the range of 2-2.5 cN/tex.

The absorption of an alginate/chitosan composite fibre produced according to the method of this invention may lie in the range from 16.3-35 (g/g) for water and 11.5-12.1 (g/g) for saline. The fibres diameter may also enlarge dramatically upon exposure to either water or saline solutions. Corresponding values for calcium alginate fibres may be 3-7 (g/g) water and 4-9 (g/g) saline, while chitosan fibres may be found to take up 2-3 (g/g) water and 1-5 (g/g) saline. Alginate/chitosan fibres produced by a core/sheath coating method according to the methods described in International Application Number PCT/GB2004/000950 may have an uptake of 11-12.5 (g/g) water and 7-9 (g/g) saline.

The produced fibres may have distinctive morphological characteristics i.e. rough/rouged surface with near perfect uniformity resembling surface characteristics of wool fibres. These features may be distinctly different to those of pure alginate or chitosan fibres and to the core/sheath fibres obtained by coating of alginate fibres using hydrolysed chitosan.

The fibre properties may be manipulated by including other additives to enhance performance and functional requirements. Examples of additives that may be incorporated into the fibres of the invention either during the production of the fibres or by subsequent post treatment are antimicrobial agents such as silver ions, chlorhexidine or any antibiotic drug, agents known to influence wound healing such as zinc ions, aloe vera or salts of hyaluronic acid and fragrances such as lavender or oil of rosemary.

According to a sixth aspect of the present invention there is provided a method of producing a composite fibre or film of alginate and chitosan, said method comprising the step of contacting a solution of alginate with a solution of chitosan.

The method may comprise a method of producing a composite fibre.

Suitably, the method comprises a method of producing a composite fibre of alginate and chitosan, said method comprising the step of releasing a solution of one of alginate or chitosan directly into a bath of the other of alginate or chitosan solution.

The method may comprise any feature as described in relation to the fifth aspect.

The method may alternatively comprise a method of producing a composite film.

The method may comprise forming a film of one of alginate or chitosan solution on a supporting surface and immersing the film in the other of alginate or chitosan solution to produce a composite film.

Suitably, the alginate solution comprises sodium alginate.

Suitably, the chitosan solution comprises chitosan that has been subjected to a controlled degree of disruption.

Suitably, the method comprises forming a film of alginate solution on a supporting surface and immersing the alginate film in chitosan solution to produce a composite film.

Alternatively, the method may comprise forming a film of chitosan solution on a supporting surface and immersing the chitosan film in alginate solution to produce a composite film.

Once formed the composite film may be washed. The film may be produced and/or processed according to any feature described in relation to the fibre forming method of the fourth aspect except where such features are mutually exclusive.

According to a seventh aspect of the present invention there is provided a composite film comprising alginate and chitosan.

Suitably, the film is produced according to the film forming method of the fifth aspect.

BRIEF DESCRIPTION OF THE DRAWINGS

The invention will now be described by way of example with reference to the accompanying drawings in which:

FIG. 1 shows a fibre forming apparatus 1 comprising a first 2, second 3, third 4, fourth 5 and fifth 6 bath positioned substantially one above the other. The apparatus 1 further comprises a dope tank 7 containing an alginate solution (spinning dope) (not shown). The alginate solution is pumped, under pressure, through a spinneret 8 located in the first bath 2. The first bath 2 contains a hydrolysed chitosan solution 9. As the alginate solution is extruded into the chitosan solution composite fibres 10 are produced.

Figure 1:
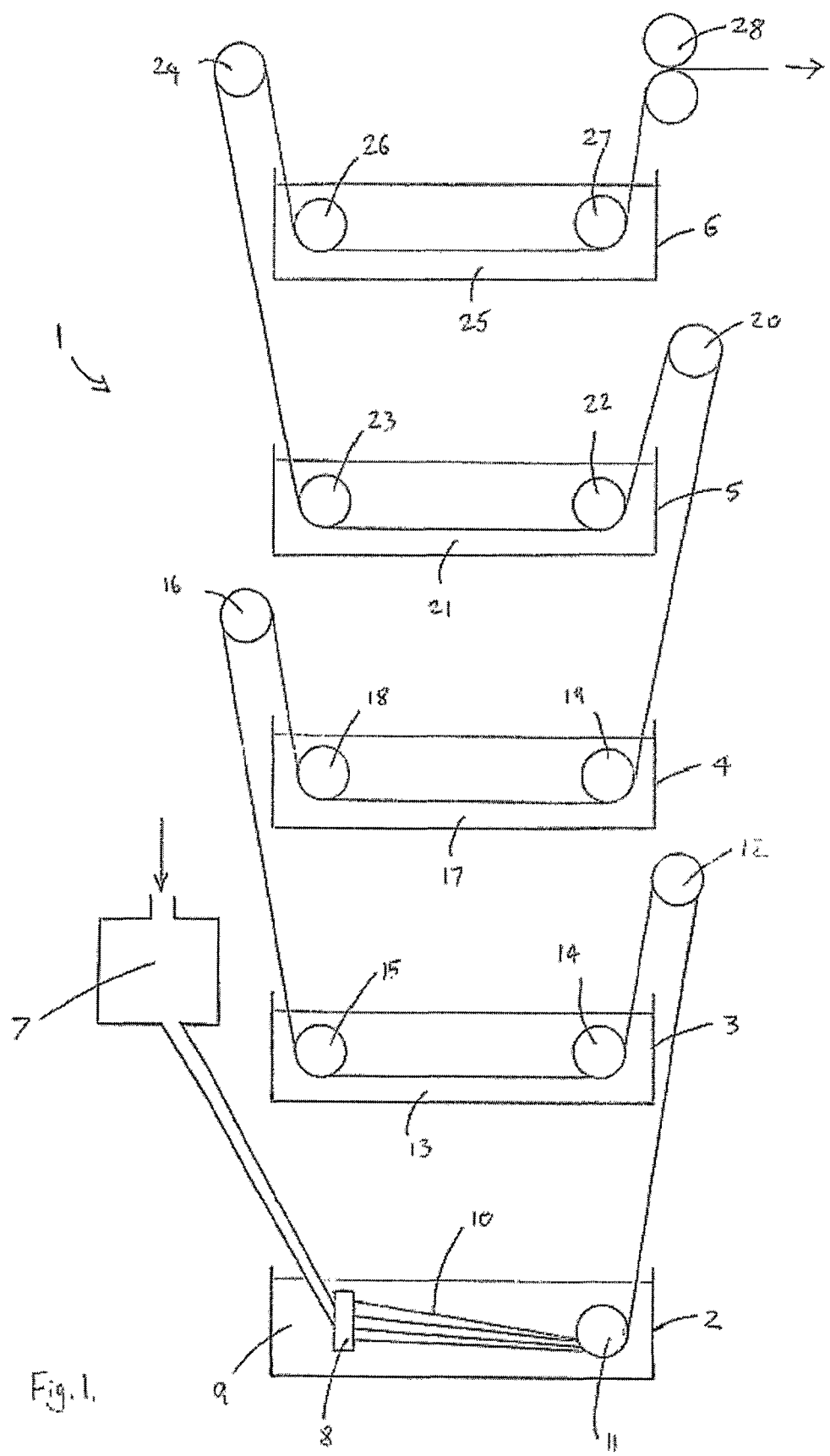
FIG. 1 is a schematic representation of one embodiment of the present invention.

The fibres 10 are drawn from the spinneret 8 via a set of rollers 11, said rollers also being located in the first bath 2. The fibres 10 travel from the first bath 2 to a second bath 3 in a substantially vertical manner via a second set of rollers 12. The fibres 10 pass through the second bath 3, the second bath 3 containing water 13 at 50-60° C. Passage of the fibres 10 through the second bath 3 is facilitated by rollers 14 and 15 located in the bath 3.

The fibres 10 travel from the second bath 3 to a third bath 4 via a third set of rollers 16. The fibres 10 pass through the third bath 3, the third bath containing a acetone-water solution 17 comprising 50% acetone. Passage of the fibres 10 through the third bath 4 is facilitated by rollers 18 and 19 located in the bath 4.

The fibres 10 travel from the third bath 4 to a fourth bath 5 via a fourth set of rollers 20. The fibres 10 pass through the fourth bath 5, the fourth bath containing a acetone-water solution 21 comprising 70% acetone. Passage of the fibres 10 through the fourth bath 5 is facilitated by rollers 22 and 23 located in the bath 5.

The fibres 10 travel from the fourth bath 5 to a fifth bath 6 via a fifth set of rollers 24. The fibres 10 pass through the fifth bath 6, the fifth bath containing acetone 25 (100%). Passage of the fibres 10 through the fourth bath 5 is facilitated by rollers 26 and 27 located in the bath 5. The fibres 10 then leave the fifth bath 6 and pass through a sixth set of rollers 28 in order to remove excess liquid. After passing through the sixth set of rollers 28 the fibres 10 are dried (not shown).

The present invention will now be described further by way of example with reference to the following examples. Examples 1 to 3 describe processing techniques and parameters used to produce composite fibres.

EXAMPLE 1

24 g of chitosan (supplied by Kate International, India) was dissolved in 600 ml of deionised water containing 1% v/v of acetic acid. The solution was stirred for 5 hours until a viscous solution was obtained. 19.8 ml of concentrated hydrochloric acid (approximately 3% w/v) was added to the solution and stirring continued for a further hour. The solution was then heated under reflux for 8.5 hours and subsequently allowed to cool. Viscosity and pH values were noted before and after hydrolysis. i.e. pH was unchanged before and after hydrolysis ~3 and viscosity dropped from 480 cP to 50 cP.

The average molecular weights of the chitosan before hydrolysis were: $M_n$ 144.5; $M_w$ 993.2; $M_z$ 2666.7; $M_{z+1}$ 4338.4; and $M_v$ 813.6. All quoted values are in KDa and were measured by GPC chromatographic analysis.

After hydrolysis the average molecular weights of the chitosan were: $M_n$ 7.3; $M_w$ 32.3; $M_z$ 121.2; $M_{z+1}$ 256.0; and $M_v$ 25.8. All quoted values are in KDa and were measured by GPC chromatographic analysis.

Sodium alginate dope solution 6% (w/v) in deionised water was prepared (using Protanal LF 10/60 with a high guluronic ratio (ManA 25-35%, GulA 65-75%) supplied by Pronova, Norway) and degassed prior to extrusion into the prepared chitosan bath. Extruded fibres were drawn, washed in warm water and passed through acetone water mixtures of increasing acetone concentrations of 50%, 70% and 100% before being dried by hot air. The properties of the fibres when tested were tenacity of 3.3-6.0 cN/tex, elongation at break 5.3-12.4%, water absorption 16.3-35 g/g and saline absorption 11.5-12.1 g/g.

EXAMPLE 2

Chitosan and alginate solutions are prepared as in Example 1 and ~1% calcium chloride/sodium hydroxide was added to the chitosan solution prior to extrusion. This lead to fibres with modified physical and mechanical properties. The properties of the fibres when tested were tenacity of 2.8-7.3 cN/tex, elongation at break 4-19.5%, water absorption 18.2-33.2 g/g and saline absorption 10.5-18.2 g/g.

EXAMPLE 3

42.6 g of chitosan (supplied by Kate International, India, as used in Example 1) was dissolved in 1 litre of water and 10 cm$^3$ of acetic acid and vigorously stirred for 4-5 hours. 33 cm$^3$ of concentrated hydrochloric acid (approximately 3% w/v) was then added and stirring continued for a further hour. This was then hydrolysed as described in Example 1 and prepared alginate dope was extruded into the hydrolysed bath. This was subsequently drawn and washed before drying by hot air. Recorded fibre properties were similar to those in Example 1.

EXAMPLE 4A

Chitosan-alginate fibres were extruded by a wet spinning process. An alginate dope was spun into a hydrolysed chitosan bath drawn and washed as per the method illustrated by FIG. 1 to produce fibres. The bath solution had a pH of 1.2, a viscosity of around 60 centipoises and comprised a 3.84% (w/v) chitosan solution hydrolyzed for eight and a half hours. Fibres were obtained for draw ratios of 1.08, 1.15 and 1.23 respectively.

The chitosan solution used in this example was prepared by dissolving 24 g of chitosan in 600 ml of deionised water containing 1% v/v of acetic acid. The solution was subsequently stirred for 5 hours until a viscous solution was obtained. 25 ml of concentrated hydrochloric acid (approximately 3.5% w/v) was added to the solution and stirring continued for a further hour. The solution was then heated under reflux for just over 8.5 hours and subsequently allowed to cool. Viscosity and pH values were noted before and after hydrolysis. i.e. pH was unchanged before and after hydrolysis 1.2 and viscosity dropped from 480 cP to 60 cP.

Sodium alginate dope solution 6% (w/v) in deionised water was prepared (using Protanal LF 10/60 with a high guluronic ratio (ManA 25-35%, GulA 65-75%) supplied by Pronova, Norway) and degassed prior to extrusion into the prepared chitosan bath.

EXAMPLE 4B

To examine the effect of small quantities of calcium chloride on the chitosan-alginate fibres the method of Example 4A was followed but this time CaCl$_2$ was added to the chitosan solution following hydrolysation. Alginate dope was then extruded into a coagulation bath of 1% hydrolysed chitosan (w/v) with 0.2% CaCl$_2$ (w/v) solution. The fibres were obtained for draw ratios of 1.08, 1.15 and 1.23 respectively.

EXAMPLE 4C

To further examine the effect of small quantities of calcium chloride on the chitosan-alginate fibres the method of Example 4A was followed but this time CaCl$_2$ was added to the chitosan solution following hydrolysation. Alginate dope was extruded into a coagulation bath of 1% hydrolysed chitosan (w/v) with 0.3% CaCl$_2$ (w/v) solution. Fibres were obtained for draw ratios of 1.08, 1.15 and 1.23 respectively.

EXAMPLE 4D

As a comparative example, the method of Example 4A was replicated but this time the alginate dope was extruded into a bath of 1.0% CaCl$_2$ solution to produce calcium alginate fibres. Fibres were obtained for draw ratios of 1.15, 1.23 and 1.31 respectively.

Tables 1, 2 and 3 indicate the results obtained for the fibres of Example 4.

TABLE 1

| Example | Coagulation Bath | Draw Ratio | Fibre Diameter (μm) | Linear Density (tex) |
|---|---|---|---|---|
| 4D (Comparative) | 1.00% CaCl$_2$ solution | 1.15 | 36.5 | 6.1 |
|  |  | 1.23 | 30.0 | 5.6 |
|  |  | 1.31 | 30.0 | 5.2 |
| 4A | Hydrolyzed chitosan (C1) | 1.08 | 37.2 | 14.0 |
|  |  | 1.15 | 58.6 | 13.4 |
|  |  | 1.23 | 50.41 | 18.7 |
| 4B | C1 + 0.20% CaCl$_2$ solution | 1.08 | 52.4 | 25.4 |
|  |  | 1.15 | 55.0 | 22.9 |
|  |  | 1.23 | 41.90 | 18.2 |
| 4C | C1 + 0.30% CaCl$_2$ solution | 1.08 | 59.0 | 22.5 |
|  |  | 1.15 | 59.0 | 22.8 |
|  |  | 1.23 | 61.2 | 18.3 |

Table 1 illustrates that generally the calcium alginate fibres are finer than the chitosan alginate fibres as indicated by the fibre diameter and linear density. The increase in the size of the chitosan alginate fibres can be attributed to the presence of the chitosan. The general bulkiness could be attributed to the bonding taking place between alginate and chitosan components. It can also be seen that the introduction of calcium chloride into the bath resulted in heavier fibres. Calcium chloride is believed to encourage more interaction between the chitosan and alginate though the mechanism is unclear at present.

TABLE 2

| Example | Coagulation Bath | Draw Ratio | Water Retention [g/g] | Saline Retention [g/g] | Fibre Diameter Swell ratio |
|---|---|---|---|---|---|
| 4D (Comparative) | 1.00% CaCl$_2$ solution | 1.15 | 9.9 | 6.5 | 1.6 |
|  |  | 1.23 | 9.7 | 7.1 | 1.4 |
|  |  | 1.31 | 4.3 | 6.1 | 1.6 |
| 4A | Hydrolyzed chitosan (C1) | 1.08 | 22.5 | 12.1 | 3.6 |
|  |  | 1.15 | 35.0 | 12.0 | 2.3 |
|  |  | 1.23 | 16.3 | 11.5 | 2.0 |
| 4B | C1 + 0.20% CaCl$_2$ solution | 1.08 | 18.2 | 11.7 | 2.5 |
|  |  | 1.15 | 18.2 | 10.5 | 2.4 |
|  |  | 1.23 | 26.2 | 15.3 | 4.5 |
| 4C | C1 + 0.30% CaCl$_2$ solution | 1.08 | 23.3 | 12.2 | 3.0 |
|  |  | 1.15 | 33.2 | 14.3 | 4.4 |
|  |  | 1.23 | 33.1 | 18.2 | 2.0 |

Figure 2:
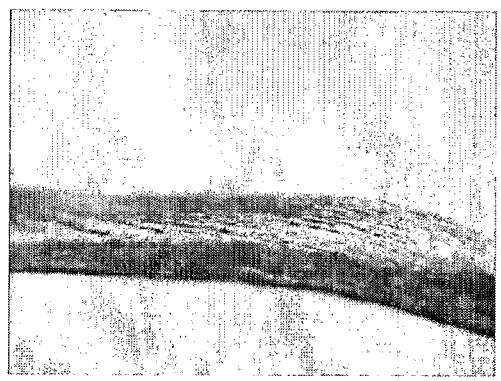
FIG. 2 is an optical image of a chitosan-alginate fibre.
Figure 3:
FIG. 3 is an optical image of a swollen chitosan-alginate fibre.

FIGS. 2 and 3 are optical images showing a chitosan-alginate fibre of Example 4A before swelling (FIG. 2) and after swelling (FIG. 3) at 200 times magnification. This and the results of Table 2 clearly indicate the absorption properties of fibres of preferred embodiments of the present invention. The fibres multiplied in diameter by as much as four and a half times with the least absorbent still multiplying by twice their original diameter. Table 1 also shows that the fibres may retain many times their own weight of water. It was also observed that fibres swelled up within around three seconds indicating a very high and ready ability to absorb liquid.

TABLE 3

| Example | Coagulation Bath | Draw Ratio | Elongation (%) | Tenacity (cN/tex) | Work to Rupture (cN*cm) |
|---|---|---|---|---|---|
| 4D (comparative) | 1.00% CaCl$_2$ solution | 1.15 | 2.9 | 4.7 | 0.1 |
| | | 1.23 | 4.6 | 5.4 | 0.2 |
| | | 1.31 | 6.1 | 10.5 | 0.5 |
| 4A | Hydrolyzed chitosan (C1) | 1.08 | 5.3 | 3.3 | 0.3 |
| | | 1.15 | 15.5 | 6.0 | 2.0 |
| | | 1.23 | 12.4 | 4.7 | 2.1 |
| 4B | C1 + 0.20% CaCl$_2$ solution | 1.08 | 4.0 | 3.3 | 0.4 |
| | | 1.15 | 14.7 | 3.7 | 2.6 |
| | | 1.23 | 19.5 | 7.3 | 4.0 |
| 4C | C1 + 0.30% CaCl$_2$ solution | 1.08 | 8.0 | 4.0 | 0.9 |
| | | 1.15 | 6.7 | 2.8 | 0.4 |
| | | 1.23 | 9.8 | 4.7 | 1.4 |

Table 3 illustrates that fibres of preferred embodiments of the present invention have a tenacity which is sufficiently high to enable them to function as textile fibres and wound dressing fibres.

Table 3 also shows that the elongation at break and work to rupture values of the fibres of preferred embodiments of the present invention were suitably high. The fibres of Example 4C had particularly high work to rupture value.

Fibres of Examples 4A, 4B, 4C and 4D were studied with a scanning electron microscope and the images are shown in FIGS. 4 to 7.

Figure 4:
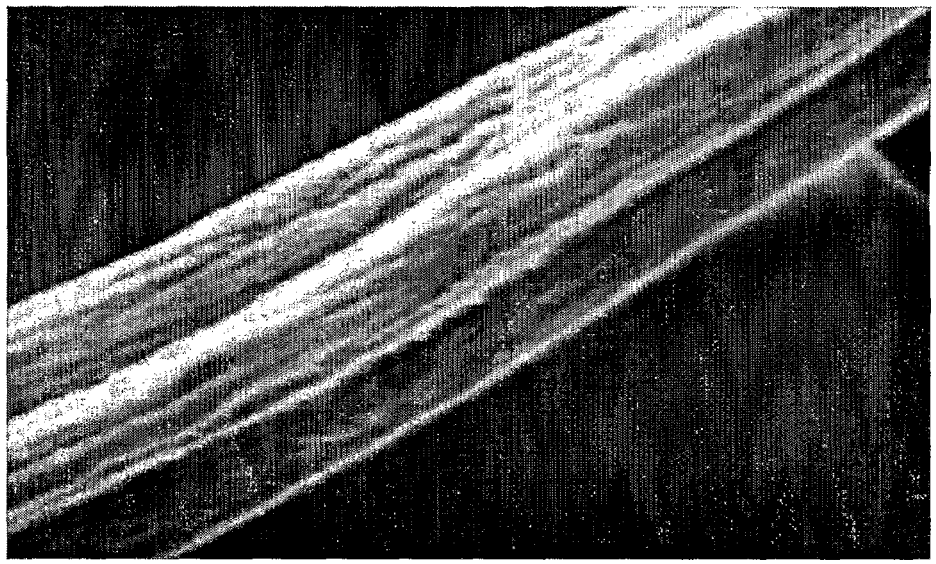
FIG. 4 is a SEM image of a chitosan-alginate fibre.

FIG. 4 is an image of the Fibre of Example 4A (draw ratio 1.15) with the image details being: 905×50 UM; 10 Kv; and WD: 10 MM.

Figure 5:
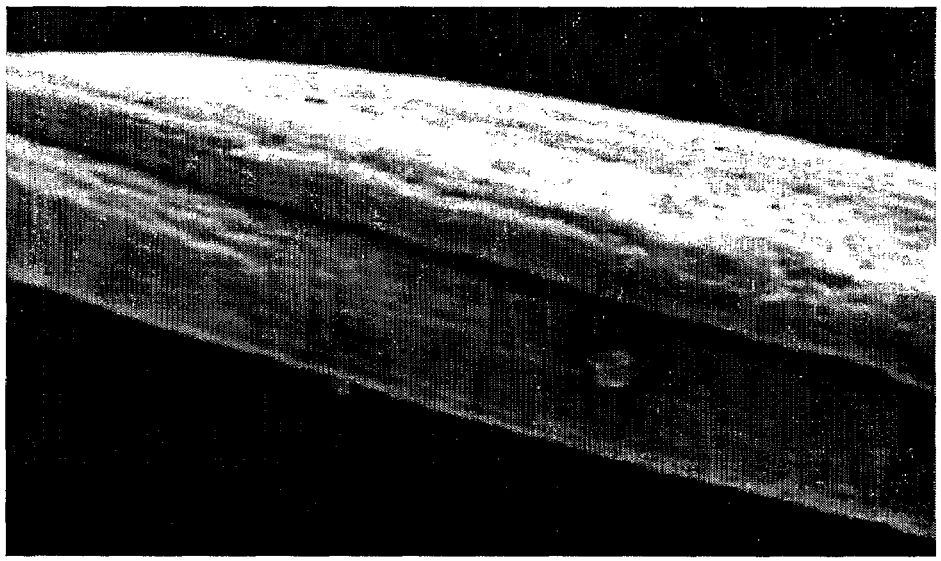
FIG. 5 is a SEM image of a chitosan-alginate fibre produced in presence of 0.2% (w/v) calcium chloride.

FIG. 5 is an image of the Fibre of Example 4B (draw ratio 1.15) with the image details being: 710×50 UM; 10 Kv; and WD: 9 MM.

Figure 6:
FIG. 6 is a SEM image of a chitosan-alginate fibre produced in presence of 0.3% (w/v) calcium chloride.

FIG. 6 is an image of the Fibre of Example 4C (draw ratio 1.15) with the image details being: 869×50 UM; 10 Kv; and WD: 9 MM.

Figure 7:
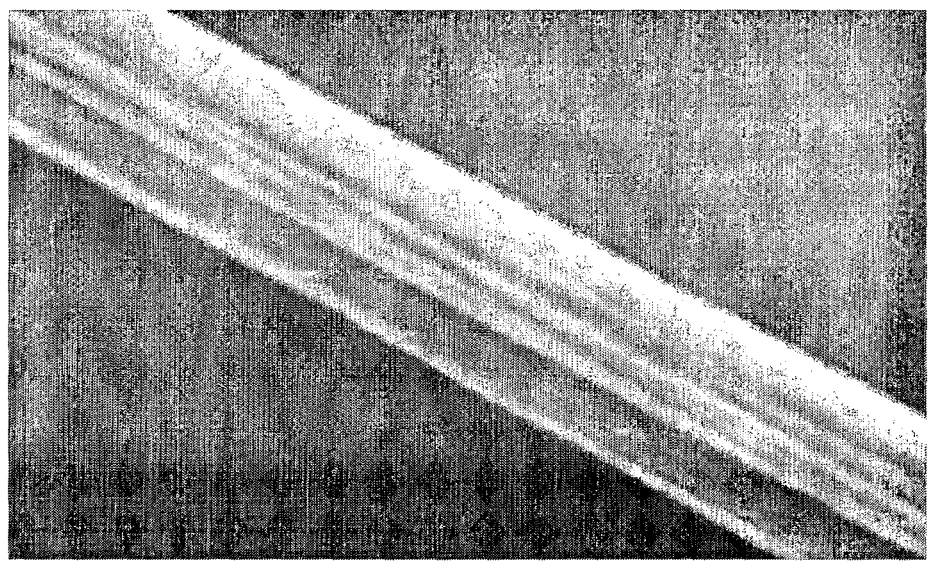
FIG. 7 is a SEM image of a calcium alginate fibre for comparison.

FIG. 7 is an image of the Fibre of Example 4D (draw ratio 1.15) with the image details being: 929×50 UM; 10 Kv; and WD: 11 MM.

It can be seen from FIGS. 4 to 7 that the calcium alginate fibres (FIG. 7) showed very smooth surface relative to the chitosan-alginate fibres (FIGS. 4 to 6). This is an indication of homogeneity of the calcium alginate fibre. The chitosan-alginate fibres showed a rugged and yet homogeneous blend of the constituent alginate and chitosan components.

The Fibres of Example 4 were studied by FT IR spectral analysis together with a sample of pure chitosan powder. In all the fibres, the differences in draw ratio were found not to significantly affect their infrared spectrogram.

All fibres showed peaks at 1070 cm$^{-1}$ which corresponds to C—O stretching bands. The characteristic peak of alginates was seen in the calcium alginate fibre spectra at 1644 cm$^{-1}$ corresponding to Carbonyl (C=O) bond or carbonyl stretching in amide I as well as amino group (1173 cm$^{-1}$). The pure chitosan powder spectra showed characteristic bands of amide I (1628 cm$^{-1}$) and amino group (1170 cm$^{-1}$). In the chitosan-alginate spectrum, the amide peak shifted to 1650 cm$^{-1}$, while the 1173 cm$^{-1}$ amino peak was absent. The calcium alginate fibres showed peaks at 1520. This peak is completely absent from chitosan-alginate. This however shifts to 1528 cm$^{-1}$ in the chitosan-alginate spectra. This is believed to indicate amide II (C—N) which usually occurs at about 1570 cm$^{-1}$. The IR spectra of calcium alginate showed absorption bands at 3472 cm$^{-1}$ representing Hydroxyl stretching. The chitosan powder showed a hydroxyl stretch at 3433 cm$^{-1}$. The OH stretching of the chitosan-alginate fibre shifted to 3444 cm$^{-1}$ which is prominent and relatively isolated as in the calcium alginates and pure chitosan.

Three new peaks appeared in the chitosan-alginate fibres' spectra which were conspicuously absent from either of the pure chitosan or calcium alginate spectra. The chitosan-alginate fibres showed peaks at 1680 cm$^{-1}$, 1720 cm$^{-1}$ and at 2878 cm$^{-1}$ (believed to be a C—H stretching peak).

The 2878 cm$^{-1}$ peak intensified with the addition of calcium chloride in the coagulation bath. This tends to equally indicate the formation of new intermolecular bonds that were non-existent in the calcium alginate fibres. It suggest the formation of the chitosan-alginate complex as a result of the ionic interaction between the negatively charged carbonyl group (—COOH) of alginate and the positively charged amino group (—NH$_2$) of chitosan. Other bonds might have been formed in the process.

An analysis was performed on chitosan-alginate fibres as in example 4A (draw ratio 1.15) to determine their Carbon, Hydrogen and Nitrogen content so as to determine the percentage by weight of chitosan in the chitosan-alginate fibre. The Chitosan content was calculated to be in the range of 1.96% to 4.50% w/w. This value was arrived at using the analytical results of Table 4 by the process outlined following Table 4.

TABLE 4

CHN Analysis results:

| Element | Analysis 1 | Analysis 2 | Mean ± SD (% correlation) |
|---|---|---|---|
| Carbon (% w/w) | 32.38 | 32.41 | 32.40 ± 0.02 (0.1%) |
| Hydrogen (% w/w) | 4.27 | 4.20 | 4.24 ± 0.05 (1.2%) |
| Nitrogen (% w/w) | 0.31 | 0.17 | 0.24 ± 0.10 (41.2%) |

[SD = standard deviation, % correlation = 100 × (SD/mean)]

Chitin (fully N-acetylated, i.e. degree of acetylation=1.00) has a nitrogen content of 6.89% w/w.

Chitosan (fully de-N-acetylated, i.e. degree of deacetylation=1.00, degree of acetylation=0.00) has a nitrogen content of 8.69% w/w.

Using these values for the standards and the nitrogen levels in the sample a chitosan content in the fibre was calculated to be 1.96-4.50% w/w, derived as follows:

Minimum chitosan value=100×(0.17/8.69)=1.96%

Maximum chitosan value=100×(0.31/6.89)=4.50%

The estimated fibre chitosan contents assume that any measured nitrogen arises solely from hydrolysed chitosan anhydro-GlcN/GlcNAc residues and not from any residual protein present in either the alginate or chitosan starting materials.

It will be appreciated by those skilled in the art that preferred embodiments of the present invention may provide a bicomponent fibre of alginate and chitosan that has desirable physical properties and good processability.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A composite fibre suitable for use in wound management products comprising alginate polymer and chitosan polymer bonded along a length of the fibre,
   wherein the fibre is produced by extruding a solution of sodium alginate directly into a coagulation bath of chitosan that has been subjected to a controlled degree of disruption achieved by hydrolysis;
   wherein the chitosan comprises at least 1% by weight of the fibre and the alginate comprises at least 75% by weight of the fibre; and
   wherein the tenacity of the fibre lies in the range of 2.8 to 10.5 cN/tex; and
   wherein the fibre is not in the form of a substrate and a coating.

2. The composite fibre suitable for use in wound management products according to claim 1, wherein the ratio of alginate:chitosan remains substantially constant along the fibre length.

3. The composite fibre suitable for use in wound management products according to claim 1, wherein the fibre comprises a bicomponent fibre of alginate and chitosan.

4. The composite fibre suitable for use in wound management products according to claim 1, wherein the fibre comprises both the alginate and chitosan polymers throughout the length and a cross section of said length.

5. The composite fibre suitable for use in wound management products according to claim 1, wherein the fibre can absorb and/or retain at least 10 times its weight of water.

6. The composite fibre suitable for use in wound management products according to claim 1, wherein the fibre comprises a plurality of fibres.

7. A method of producing a composite fibre comprising extruding a solution of alginate directly into a coagulation bath of chitosan solution of chitosan that has been subjected to a controlled degree of disruption, achieved by hydrolysis and
   wherein the method comprises forming a fibre comprising alginate polymer and chitosan polymer along a length of the fibre;
   wherein the chitosan comprises at least 1% by weight of the fibre and the alginate comprises at least 75% by weight of the fibre;
   wherein the tenacity of the fibre lies in the range of 2.8 to 10.5 cN/tex; and
   wherein the fibre is not in the form of a substrate and coating.

8. The method of producing the composite fibre according to claim 7, wherein the chitosan is in aqueous solution of calcium chloride and/or sodium hydroxide in an amount of up to around 2% (w/v).

9. The method of producing the composite fibre according to claim 7, wherein the composite fibre formed in the fibre forming step is subjected to a washing operation.

10. The method of producing a composite fibre according to claim 7, wherein the ratio of alginate and chitosan remains substantially constant along a length of the fibre.

* * * * *